United States Patent [19]
Ishikawa et al.

[11] Patent Number: 6,063,564
[45] Date of Patent: May 16, 2000

[54] CIRCULATION THIN LAYER LIQUID PHASE ASSAY

[75] Inventors: Eiji Ishikawa, 24-1, Ohtsukadainishi 3-chome, Miyazaki-shi, Miyazaki 880-2105; Setsuko Ishikawa, Miyazaki, both of Japan

[73] Assignees: Sumitomo Pharmaceuticals Company Limited, Osaka; Eiji Ishikawa, Miyazaki, both of Japan

[21] Appl. No.: 09/124,767

[22] Filed: Jul. 30, 1998

[30] Foreign Application Priority Data

Jul. 31, 1997 [JP] Japan ................................. 9-220956

[51] Int. Cl.[7] ..................................................... C12Q 1/70
[52] U.S. Cl. .................................................................. 435/5
[58] Field of Search ................................. 435/5, 7.1, 7.9, 435/7.91, 7.92, 7.93, 7.94, 7.95, 974, 975; 436/518, 523, 524, 531

[56] References Cited

U.S. PATENT DOCUMENTS 4,320,087  3/1982  Chau et al. ................................ 422/69

OTHER PUBLICATIONS

Setsuko Ishikawa et al., "Ultrasensitive and Rapid Enzyme Immunoassay (Thin Aqueous Layer Immune Complex Transfer enzyme Immunoassay) for antibody IgG to HIV–1 p17 Antigen", *Journal of Clinical Laboratory Analysis*, vol. 12, 1998, pp. 179–189.

*Primary Examiner*—Jeffrey Stucker
*Attorney, Agent, or Firm*—Sughrue, Mion, Zinn, Macpeak & Seas, PLLC

[57] ABSTRACT

An assay method capable of efficiently trapping an analyte in a certain amount of a reaction liquid in a short reaction time, the method being characterized in that only a part of a solid phase coated with a substance that specifically binds to the substance to be assayed is immersed in a pool of the reaction liquid containing the analyte, and this part of the solid phase is exchanged during the reaction, so that any surface of the solid phase can be immersed in the reaction liquid once in a predetermined time, and an assay kit for the assay based on this principle. In comparison with the conventional assay methods wherein the entire area of a limited solid phase surface is brought into contact with a certain amount of a reaction liquid, or wherein a test solution is diluted to bring the entirety of a certain surface area of the solid phase into contact therewith, the inventive method can increase reaction speed, which in turn results in trapping of the analyte on the solid phase efficiently in a short time. This reaction system can be used for the detection of an enzyme label in an enzyme immunoassay.

7 Claims, 6 Drawing Sheets

FIG. 1A
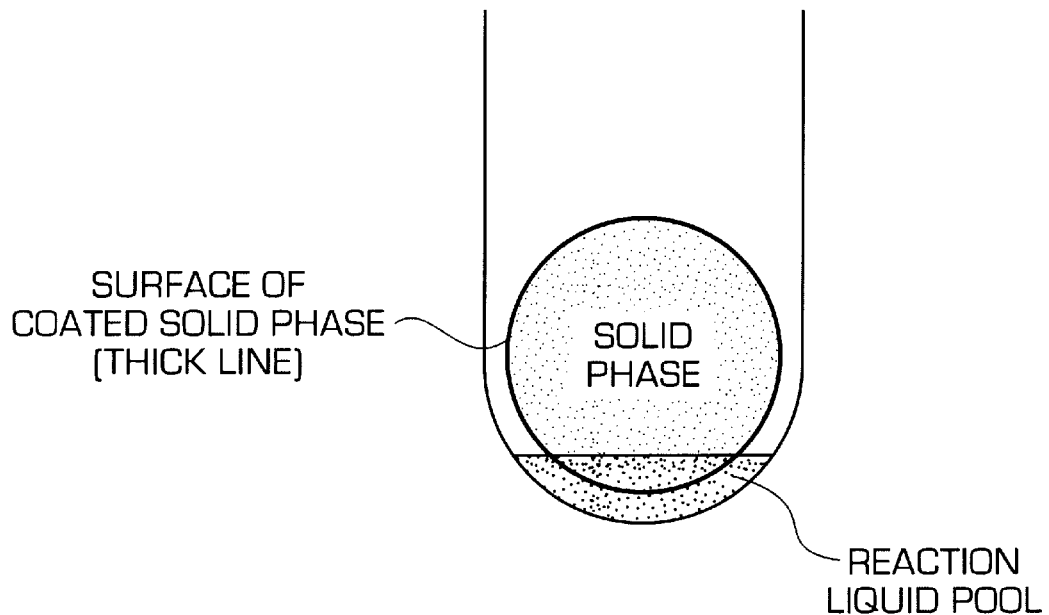
SURFACE OF COATED SOLID PHASE (THICK LINE)
SOLID PHASE
REACTION LIQUID POOL
FIG. 1B
BALL TYPE SOLID PHASE IN ROTATION DURING REACTION
FIG. 1C
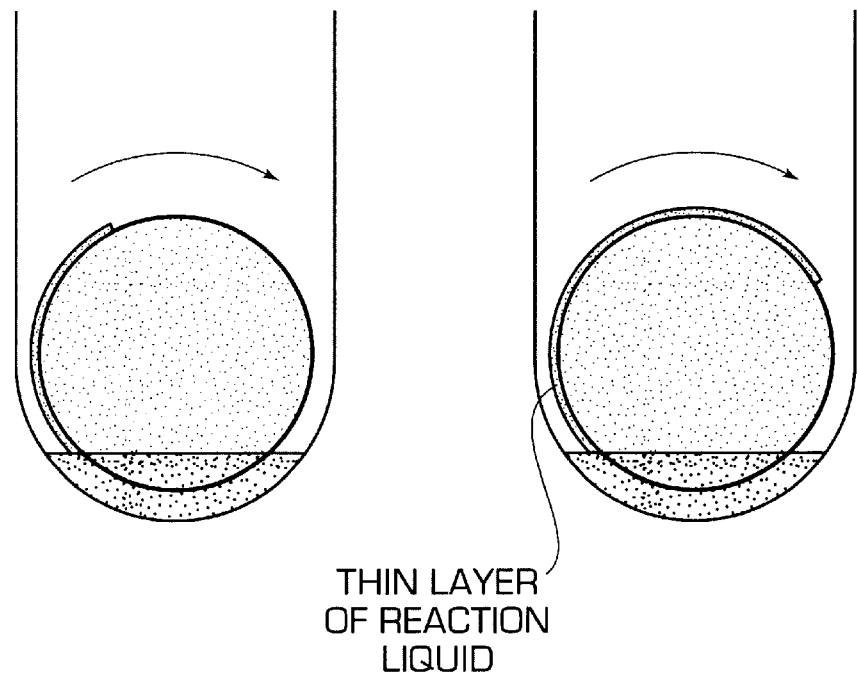
THIN LAYER OF REACTION LIQUID

SOLID PHASE

SURFACE OF COATED SOLID PHASE (THICK LINE)

REACTION LIQUID POOL

TEST TUBE TYPE SOLID PHASE IN ROTATION DURING REACTION

THIN LAYER OF REACTION LIQUID

FIG. 3A
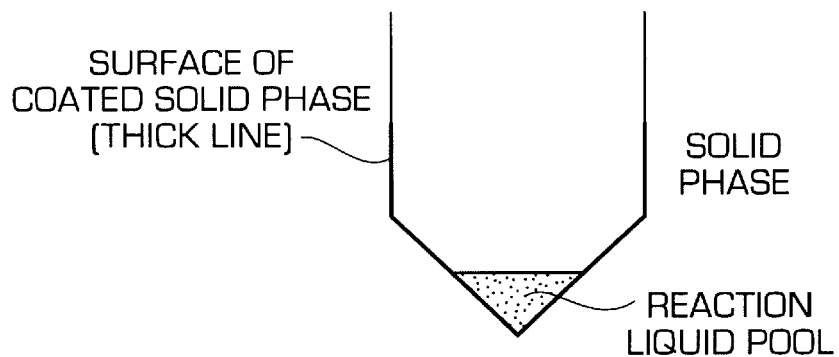
FIG. 3B
FIG. 3C
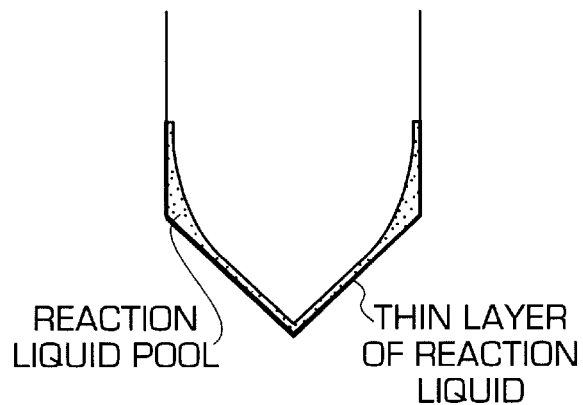
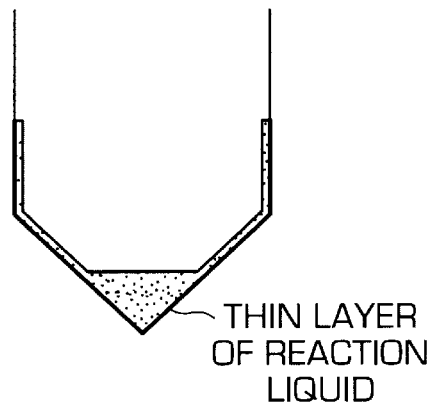
FIG. 3D
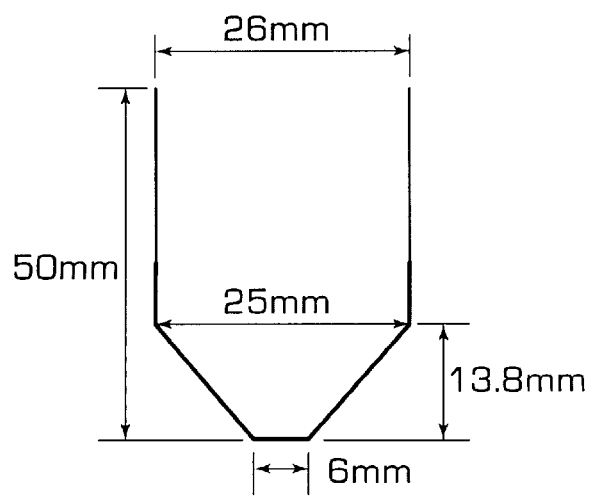

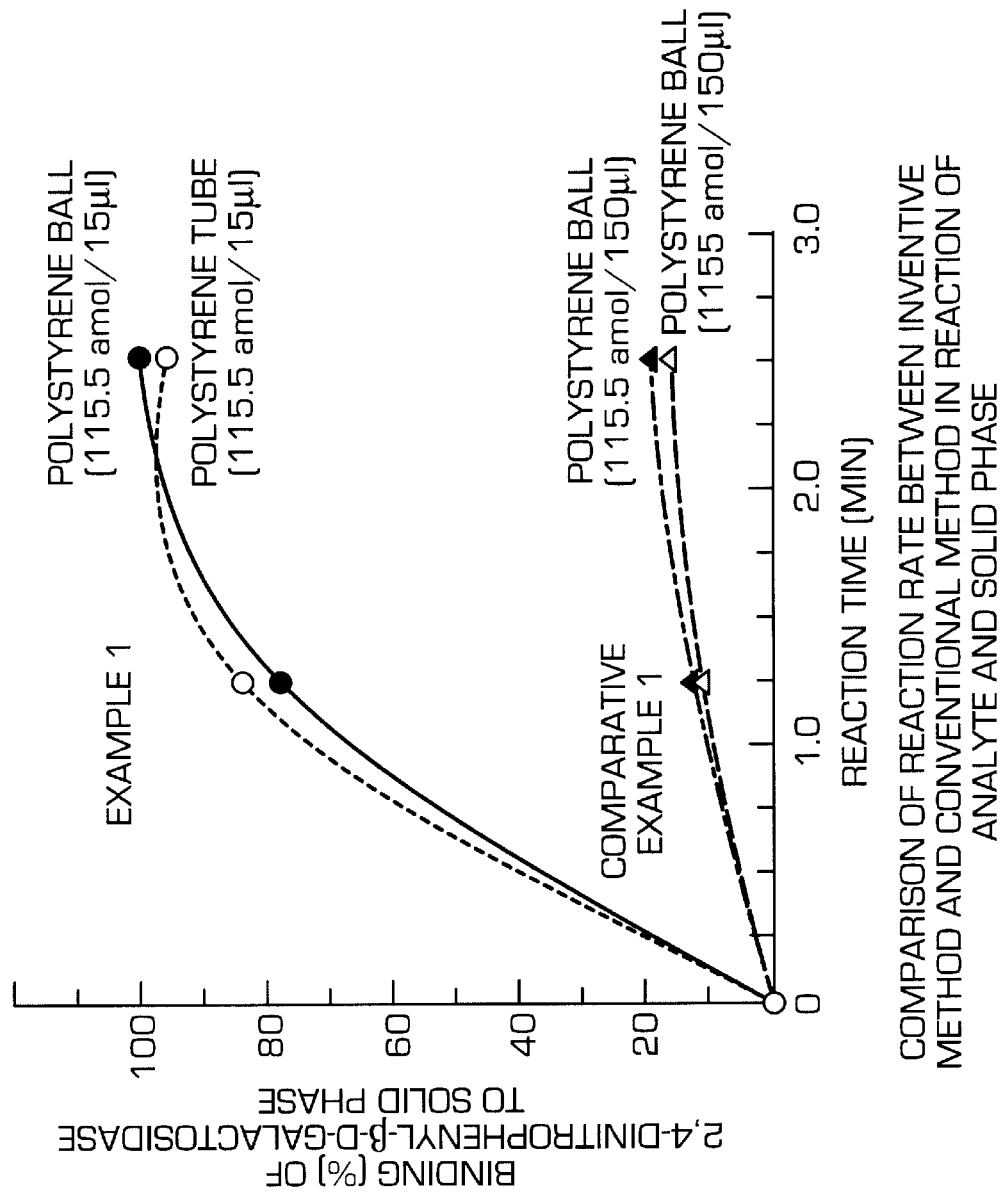

RATE OF REACTION OF ANALYTE AND CUP TYPE SOLID PHASE

COMPARISON OF REACTION RATE BETWEEN INVENTIVE METHOD AND CONVENTIONAL METHOD IN ASSAY OF HIV-1, p24 ANTIGEN

CIRCULATION THIN LAYER LIQUID PHASE ASSAY

TECHNICAL FIELD OF THE INVENTION

The present invention relates to a method for trapping an analyte on an insoluble carrier by the action of a substance that specifically binds to the analyte, and to a method for assaying the amount (concentration) of the analyze.

BACKGROUND OF THE INVENTION

A method for quantitative assay of a specific substance, which comprises trapping an analyte on an insoluble carrier (hereinafter also referred to as a solid phase) coated with a certain substance that specifically binds to the analyte and assaying the trapped analyte, has been heretofore used for assaying various substances due to its high sensitivity and high specificity. The assay system most generally used is an immunoassay wherein the surface of a solid phase is coated with an antigenic substance or antibody and allowed to react with a specific antibody or antigenic substance in a test solution, which is followed by an assay. For example, there have been documented an assay of growth hormone by Addison et al. (Addison et al., Horm. Metab. Res., 3, 59 (1971)), an assay of rat liver ornithine δ-aminotransferase by Ishikawa and Kato (Ishikawa and Kato, Scand. J. Immunol., 8(Suppl. 7), 43 (1978)) and many others.

Also frequently used is an assay method wherein a nucleic acid (polynucleotide) substance is applied to a solid phase and a nucleic acid substance in a test solution, that has a complementary sequence, is allowed to form a specific hybrid on the solid phase. For example, Virtanen et al. report on an assay of urinary cytomegarovirus (Virtanen et al., J. Clin. Microbiol., 20, 1083 (1984)) and Ranki et al. report on an assay of adenovirus in nasopharyngeal mucus (Ranki et al., Lancet, 381(1983)). In addition, an assay by binding a ligand in a test solution to a solid phase coated with a receptor (Gargosky et al., J. Endcrinol., 127, 383 (1990)) and an assay by binding a sugar chain substance to a solid phase coated with lectin molecules (Nagata A. et al., Tumour Biol., 12, 35 (1991)) have been reported.

In these assay methods, a greater area of contact between a solid phase coated with a substance that specifically binds to an analyte and a reaction liquid containing said analyte is associated with a greater amount of the analyte trapped on the solid phase per unit time, which in turn advantageously shortens the reaction time. Thus, various attempts have been made to increase the surface area of the solid phase to be in contact with a certain amount of a reaction liquid. For example, the surface area is increased by forming a wing-like protrusion in a solid phase container (French Patent No. 2697913), the surface area of a solid phase to be in contact with a reaction liquid is increased by inserting a rod that fits in a solid phase container to allow only a thin gap between the container and the rod (Japanese Patent Unexamined Publication No. 005657/1983), the total surface area is increased by the use of a microparticle solid phase (U.S. Pat. No. 4,018,886), and other methods have been reported.

However, the above-mentioned methods using a wing-like solid phase and the rod insertion method are applicable only when a special solid phase is used, and lack genera applicability. In addition, the microparticle solid phase is difficult to handle and is not suitable for manual handling, thus limiting its application to a method using an automatic device. There is an obvious limit on increasing the surface area of a solid phase to be in direct contact with a certain amount of a reaction liquid if the attempt is made using known materials and is based on operability in conventional methods. As a means for increasing the surface area of a solid phase to be in contact with a certain amount of a test solution, the test solution may be diluted with a suitable solvent to increase the total amount of the reaction liquid. In this case, the analyte is also diluted to have a lower concentration, thereby degrading reaction efficiency, so that the reaction time is not sufficiently shortened.

What has caused the artisan to stick to the above-mentioned concepts is the fixed idea that a reaction liquid should always be in homogeneous contact with the surface of a solid phase to satisfy assay precision in conventional solid phase assays. In other words, it has been generally accepted that a failure of even a part of the solid phase to be in contact with the reaction liquid would result in the absence of the reaction which is supposed to occur on said part, thereby making the reaction heterogeneous during the assay, and that, in the absence of contact with the liquid, said part will dry and the substance that specifically binds to the analyte on the solid phase will be inactivated, which will ultimately lead to insufficient assay accuracy due to the degraded binding property or release of the binding substance. The common knowledge that a solid phase should be completely immersed in a sufficient amount of liquid has been also accepted in the case of an enzyme reaction system for enzyme immunoassay (EIA), wherein an enzyme-labeled analyte is trapped on a solid phase and detected via an enzyme reaction. That is, an "enzyme label-analyte-carrier" during use has been completely immersed in a reaction liquid containing an enzyme substrate.

It is therefore an object of the present invention to provide an easy and quick assay method that can be practiced manually using not only a special solid phase or automatic device but also an all-purpose solid phase.

SUMMARY OF THE INVENTION

In accordance with the present invention, it has now been found that, in an assay method, such as immunoassay and nucleic acid hybridization, wherein an analyte is trapped on a solid phase by the aid of a substance that specifically binds to said analyte, it is only necessary to immerse a part of the solid phase carrier in a pool of a reaction liquid and to change the part to be immersed, in order to allow the progress of the reaction in the entirety of the surface of the solid phase, as if the entire surface is in homogeneous contact with the reaction liquid, whereby one can shorten the reaction time. The principle of the present invention has been successfully applied to an enzyme reaction in an enzyme immunoassay for the detection of a label on the solid phase.

Thus, the present invention provides the following.

(1) In an assay method comprising a reaction for trapping an analyte in a reaction liquid on the surface of an insoluble carrier by the action of a substance that specifically binds to the analyte, the assay method is characterized by the following (A), (B) and (C):
 (A) a part of the surface of the carrier is immersed in a pool of the reaction liquid,
 (B) the remaining part of said surface is wet with the reaction liquid, forming a thin layer of the reaction liquid, and
 (C) the parts of (A) and (B) above are exchanged with each other during the reaction.

(2) The assay method of above (1), wherein the reaction liquid contains a test sample.

(3) In an assay method comprising trapping an analyte on the surface of an insoluble carrier, by the action of a substance that specifically binds to the analyte, inducing an enzyme into said analyte as a label, and reacting the resulting "insoluble carrier-analyte-enzyme" complex in an enzyme reaction liquid containing a substrate, the assay method characterized by the following (A), (B) and (C):

(A) a part of the surface of the carrier is immersed in a pool of the enzyme reaction liquid, (B) the remaining part of said surface is wet with the enzyme reaction liquid, forming a thin layer of the enzyme reaction liquid, and (C) the parts of (A) and (B) above are exchanged with each other during the reaction.

(4) The assay method of the above (3), wherein the enzyme is β-D-galactosidase.

(5) The assay method of the above (1) or (3), wherein the insoluble carrier is a polystyrene ball, a polystyrene test tube or a polystyrene cup.

(6) The assay method of the above (1) or (3), wherein the analyte and the substance that specifically binds thereto cause an immunoreaction (antigen-antibody reaction).

(7) The assay method of the above (6), wherein the analyte is an HIV (human immunodeficiency virus) antigen or an anti-HIV antibody and the substance that specifically binds thereto is a specific anti-HIV antibody or an HIV antigen, respectively.

(8) An assay kit for the method of the above (1) or (3).

BRIEF DESCRIPTION OF THE DRAWINGS

FIGS. 1(A)–(C) are sectional schematically showing one embodiment of the present invention.

FIGS. 3(A)–(D) are sectional schematically showing yet another embodiment of the present invention.

FIG. 4 is a graph showing the relationship of reaction time and reaction rate (percentage) of the inventive method and a conventional method using a ball type solid phase and a tube type solid phase in the reaction between an analyte contained in a certain amount of a solution and a substance on the solid phase that specifically binds to said analyte.

DETAILED DESCRIPTION OF THE INVENTION

Figure 2A:
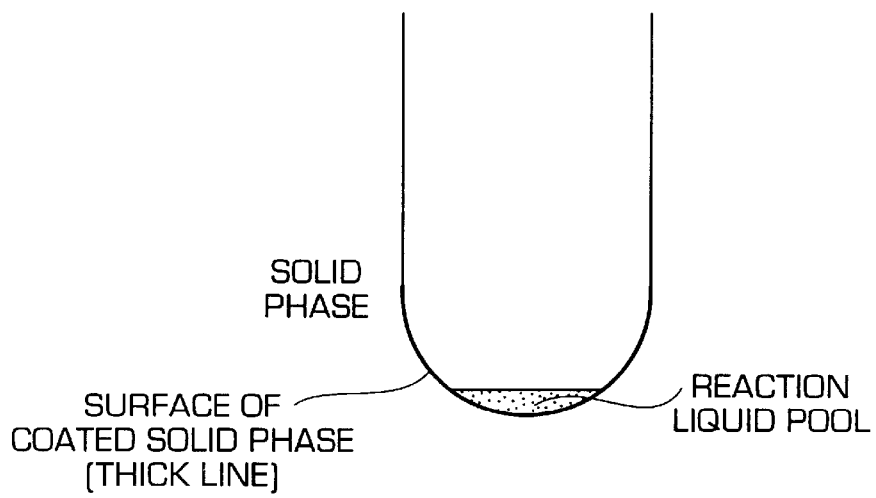
FIGS. 2(A)–(C) are sectional schematically showing another embodiment of the present invention.

The terms and definitions used in the present invention are explained in the following.

The "analyte" is not subject to any particular limitation as long as it is to be trapped on a solid phase, and is a substance capable of being assayed by a solid phase assay method such as a protein immunoassay and nucleic acid hybridization. It is exemplified by an antigen, an antibody, a nucleic acid (e.g., DNA and RNA), a sugar, a lipid and a ligand. The antigenic substance is exemplified by virus antigens such as HIV core antigen and HBV surface antigen, protein hormones such as insulin and growth hormone (GH), plasma proteins such as C-reactive protein (CRP) and fibrin degradation product, tumor markers such as α-fetoprotein (AFP) and carcinoembryonic antigen (CEA), haptens such as thyroxine and vasopressin, and various antibody specific antigens to be mentioned later. Examples of the antibody include those against the above-mentioned various antigenic substances, anti-virus antibodies such as anti-HIV antibody and anti-HBV antibody, autoantibodies such as antinuclear antibody and anti-thyroglobulin antibody, anti-protein medicament antibodies such as anti-interferon antibody and anti-growth hormone antibody, and allergen specific IgE. As the nucleic acid, DNA of genetic diseases such as phenylketonuria and familial amyloidotic polyneuropathy, RNA or DNA of pathogen such as HIV and tubercule bacillus, oncogene DNA such as N-myc of neuroblastoma and C-myc of Burkitt lymphoma are used. As the sugar, glycosylated hemoglobin A1C, hyaluronic acid and the like are used; and as the lipid, lipoprotein (a) and the like can be used. As other ligands, 1,25-dihydroxyvitamin D3 and the like can be used.

In the present invention, "assay" means quantitative determination and detection of the analytes, inclusive of reactions necessary therefor.

The "substance that specifically binds to analyte" means a substance having a selectively high affinity for the analyte. When the analyte is an antigen, specific antibodies and the like are used. When it is an antibody, antigens, antiantibodies and the like are used. When it is a nucleic acid, DNA and RNA having a complementary nucleotide sequence and the like are used In the case of a sugar, lectin and the like are used, and in the case of a ligand, a receptor and the like are used.

Thus, the analyte and the substance that specifically binds thereto can cause an immunoreaction (antigen-antibody reaction), and where the analyte is an HIV (human immunodeficiency virus) antigen or an anti-HIV antibody the substance that specifically binds thereto is a specific anti-HIV antibody or an HIV antigen, respectively.

The "insoluble carrier" means a solid phase used for trapping an analyte in a reaction liquid. This is a common knowledge in the technical field to which the inventive immunoassay pertains. The material conventionally used is exemplified by polystyrene, polyacryl, polycarbonate, polymethacrylate, Teflon, cellulose membrane, paper, glass, agarose, ferrite, latex (natural rubber) and the like. The shape of the carrier is not particularly limited and may be a bead, ball, plate, stick, gel, sheet, capsule and the like.

The technique to be used to cover the surface of a solid phase with a substance that specifically binds to an analyte may be any technique known in this field. That is, the substance that specifically binds to an analyte may be applied by physical adsorption, or may be coated by a covalent bond via an amino group or carboxyl group. A suitable application method for enhanced reactivity comprises indirect coating using one or more mediating substances such as an avidin-biotin system. An operation generally employed to prevent adsorption of non-specific substances in a reaction liquid onto a solid phase may be used and may be any conventional method. Examples of the substance to be used for this end include bovine serum albumin, gelatin, skim milk and the like.

In the present invention, the "reaction liquid" may be any one as long as it contains an analyte, and various reagents may be also contained therein in practicing the present invention. When a test sample is contained in the reaction liquid, the inventive assay method should be even more effective.

As the "test sample", biological fluids such as serum, plasma, saliva, urine, sputum, cerebrospinal fluid, lymph fluid and the like, and various buffers containing an analyte, such as a cell culture liquid, exact solution, suspension and the like may be used. When the test sample is a solid, it is made into a liquid by a known method such as dissolution, suspending, emulsification and the like, before applying the same to the assay. The test sample is a known concept in this field and any sample applicable to an assay can be used.

What is meant by "a part of the surface of a solid phase being immersed in a pool of a reaction liquid" is a co-existence of a part of the surface of a solid phase that is immersed in the pool of a reaction liquid and a part that is not so immersed during the reaction. In this context, the spool of a reaction liquid" is a part of the reaction system wherein a certain amount of a reaction liquid is retained. The "pool of a reaction liquid" can be prepared by maintaining a suitable amount of a reaction liquid in a container having a recess, such as a test tube. A solid phase which may have various shapes is placed in this pool of a reaction liquid and partially dipped therein. One typical mode is one wherein a ball type solid phase is partially immersed in a pool of a reaction liquid contained in a test tube of a suitable size is shown in FIG. 1(A). The proportion of the part partially immersed in the pool of a reaction liquid to the entirety of the solid phase surface can vary depending on the assay target and assay conditions, and is not particularly limited. Those of ordinary skill in the art will easily determine the optimal proportion. In general terms, a smaller ratio thereof is associated with a greater proportion of the surface area of the solid phase to the reaction liquid. In practice, however, a greater surface area makes it difficult to form a uniform thin layer of the reaction liquid on the surface of a solid phase. Conversely, when the ratio becomes too high, an increase in the proportion of said area relative to the volume of the reaction liquid, which characterizes the present invention, becomes less, and the effects of the present invention as evidenced by shorter reaction time and greater sensitivity are impaired. The proportion is generally preferably 5–50% for balancing practical aspects and effects. When a ball type solid phase and a pool of a reaction liquid in a test tube are used, in particular, 10–30% of the surface of the ball type solid phase is preferably immersed in the pool of a reaction liquid.

Figure 2B:
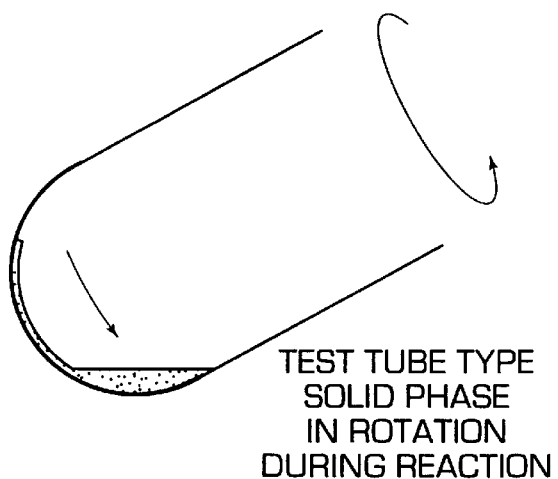
Figure 2C:
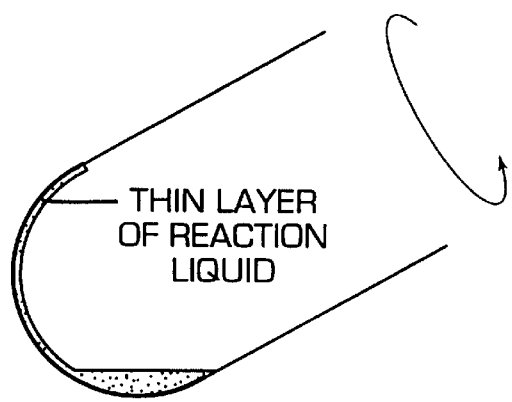

When a solid phase itself is made to have a recess, as in the case of a test tube, a pool of reaction liquid can be also held on the solid phase. In FIG. 2, a part of the surface of a solid phase (inside of the test tube) covered with a substance that specifically binds to the analyte is immersed in a reaction liquid. In FIG. 2, a solid phase having a recess is rotated about a slanted axis to form a pool of a reaction liquid and a thin layer of the reaction liquid. A cylindrical cup having a conical bottom is also a preferable embodiment as a carrier having a recess (FIG. 3). When such a cup is at a standstill, pool of a reaction liquid rests on the conical bottom. When the cup is rotated, it moves to the side of the cup due to centrifugal force. When the rotation ends, the pool of the reaction liquid again moves to the bottom. Thus, intermittent rotation of the cup causes continual changes of the pool of the reaction liquid and the thin layer of the reaction liquid, that are in contact with the surface of a solid phase. The rotation of the cup can be easily achieved by connecting the axis of a rotation motor to the bottom of the cup. Thus, this embodiment is one of the preferable modes in applying the present invention to an automatic device.

As mentioned above, the present invention is most significantly characterized by frequent exchange of the surface of a solid phase immersed in a pool of a reaction liquid (see FIGS. 1–3, (B) and (C) in each Figure). In other words, while a portion of the surface of a solid phase is immersed in a pool of a reaction liquid once in a given time period and exposed to the outside air at another time, the surface of the solid phase is always wet with the reaction liquid. In the present invention, the thin layer liquid phase means a thin layer of a reaction liquid formed on the surface of a solid phase that protrudes from the pool of a reaction liquid. During the reaction, the surface of the solid phase goes in and out from a pool of a reaction liquid (circulation) and the reaction proceeds both in the pool of the reaction liquid and in the thin layer liquid phase formed on the surface of the solid phase. Such reaction system is hereinafter referred to as a circulation thin layer liquid phase reaction system and the assay method of various assay substances using this reaction system is hereinafter referred to as a circulation thin layer liquid phase assay method.

What is to be emphasized here is that this is not a mere increase of the total surface area of the solid phase involved in the reaction that is achieved by circulating the contact site between a pool of a reaction liquid and the solid phase. A substance that specifically binds to an analyte and/or a substance used to prevent nonspecific adsorption are applied to the surface, so that the surface of the insoluble carrier generally has higher affinity for the liquid. Consequently, even if the surface is not in a direct contact with the pool of a reaction liquid, a thin layer of the reaction liquid can be maintained on the surface for a certain amount of time (FIG. 1(C)) and the reaction proceeds as in the part in direct contact with the pool of a reaction liquid. The part where the thin layer has been formed is designed to be in contact with the pool of a reaction liquid again before the analyte in the thin liquid layer binds to the solid phase to saturation, or the surface of a solid phase dries and stops reacting, such that the reaction proceeds on the entire surface of the solid phase as if it is immersed in the pool of a reaction liquid, thereby strikingly increasing the reaction speed. Therefore, by the "certain amount of time" here is meant the time up to saturation of the reaction of the analyte in the thin liquid layer on the solid phase or the termination of the reaction due to the drying of the solid phase surface, which is generally within 5 minutes, preferably within 1 minute.

While the method for realizing the environment, wherein the solid phase is always circulated, is not particularly limited, it is exemplified by the following method.

(1) Rotation, transfer and deformation of a solid phase. A solid phase is rotated or transferred by a physical means such as shaking, sting and inversion of a reaction vessel, operation by magnetic force from outside upon placing iron and the like therein, and rotation by an electric motor. The most convenient method is shaking of an incubator housing a round bottom tube having a suitable size and containing a solid phase having a rotatable shape such as a ball. In addition, a test tube type solid phase may be easily rotated about a slanted axis. A method wherein a test cup type solid phase is intermittently rotated or stood in a vertical position may be employed.

(2) Rotation, transfer and permeation of a reaction liquid. A reaction liquid is rotated or transferred by a physical means mentioned above, or by circulation of liquid using a pump or capillary phenomenon of the liquid itself.

The above-mentioned circulation thin layer liquid phase reaction system can be applied to an enzyme reaction for an enzyme labeled assay such as ELISA. To be specific, in the steps where (1) an analyte is trapped on the surface of an insoluble carrier (solid phase) coated with a substance that specifically binds to the analyte in a reaction liquid, (2) an enzyme is introduced into said analyte as a label, (3) the thus obtained "solid phase-analyte-enzyme" complex is added to a substrate solution of the enzyme, and (4) the enzyme reaction product is quantitatively determined, superior reaction efficiency can be achieved when the reaction is carried out under the conditions where (A) a part of the surface of the solid phase, on which a "solid phase-analyte-enzyme" complex has been formed, is immersed in the pool of the solution containing the enzyme substrate, (B) the other part of said surface of the solid phase is wet with the substrate solution, thus forming a thin layer of the substrate solution, and (C) said part and the other part of the surface of the solid phase of the above-mentioned (A) and (B) are exchanged with each other during the reaction. This is because binding of the enzyme substrate in the substrate solution and the enzyme on the solid phase is accelerated, like binding of the analyte and the substance that specifically binds to the analyte is accelerated. In general since the substrate for labeling enzyme is used at a concentration not more than the Km value of the enzyme, a higher substrate concentration in a normal system can increase the reaction speed. Nevertheless, an increased substrate concentration in a conventional system using a sufficient amount of substrate solution leads to a greater increase in the total amount of the substrate as well, which in turn results in greater amounts of color development or fluorescence caused by the substrate itself, thereby preventing the assay. The present invention is characterized by a lower total amount of the substrate and the reaction at a high substrate concentration. Needless to say, since the enzyme on the solid phase is designed to be in homogeneous contact with the substrate solution, the homogeneous property of the reaction and the quantitative determination performance of the reaction are not impaired. The "solid phase-analyte-enzyme" complex may be formed by any method used in a conventional enzyme immunoassay. That is, a substance that specifically binds to an analyte and that has been previously labeled with an enzyme may be used (sandwich method), or a substance that competitively reacts with the analyte and that has been previously labeled with an enzyme may be used (competitive method). In the former case, a one step method or two step method may be used, and the analyte and the substance previously labeled with an enzyme may be first reacted in a liquid phase and then trapped on the solid phase.

When practicing the inventive enzyme reaction system, the kind of enzyme for labeling, the kind of substrate and concentration thereof are subject to no particular limitation. Typically, β-D-galactosidase, peroxidase, alkane phosphatase and the like are used as the enzyme. When β-D-galactosidase is used as the enzyme, the assay method is exemplified by a method wherein the fluorescence intensity of the product, 4-methylumbelliferone, is assayed using 4-methylumbelliferyl-β-D-galactosidase as a substrate (Imagawa et al., Ann. Clin. Biochem., 21, 310 (1984)).

When practicing the assay method of the present invention, containers and reagents necessary for said circulation thin layer liquid phase reaction system are preferably set in a kit. Such kit includes, for example, an insoluble carrier coated with a substance that specifically binds to an analyte, a container for preparing a pool of reaction liquid, reagents such as a buffer, various labels introduced for the detection and the like, in necessary amounts. When the present invention is applied to an enzyme reaction system, a substrate for the enzyme is also included.

EMBODIMENT OF THE INVENTION

The inventive assay method can be performed by the following steps. One embodiment of the present invention (2 step sandwich immunoassay wherein the analyte is an antigen) is concretely explained in the following.

(1) Coating of solid phase with specific antibody

A solid phase for immunoassay, such as a polystyrene ball, is treated with an antibody solution and the antibody is physically adsorbed on the surface to prepare a solid phase.

(2) Preparation of a pool of reaction liquid

A test tube having a suitable size is charged with a buffer for immune reaction and a sample containing the analyte, to give a pool of a reaction liquid. In so doing, the amount and depth of the pool of the reaction liquid are appropriately set based on a preliminary testing. They are the least possible amounts within the range permitting making the surface of the solid phase sufficiently wet When a 6 mm diameter ball is set in a test tube having an inner diameter of 13 mm, for example, the amount of the liquid is 10–30 μl.

(3) Reaction

The solid phase prepared in (1) is added to the pool of the reaction liquid and incubated with shaking. After the reaction, the solid phase is separated from the reaction liquid and washed.

(4) Labeling

An antibody that specifically binds to the assay target antigen is previously labeled and added to the solid phase previously washed, thereby allowing binding of said labeled antibody to label the antigen trapped on the surface of the solid phase in (2). As the label, a known labeling substance can be used, such as an enzyme (e.g., β-galactosidase), an RI (e.g., radioactive iodine) and a fluorescent substance.

(5) Assay

The antigen labeled in (4) is quantitatively determined by a conventional method. For example, when an enzyme is used as label, a circulation thin layer liquid phase reaction system is used for the enzyme reaction, as in the immune reaction of the above (2), to quantitatively determine the label. When a different label is used, the inventive circulation thin layer liquid phase reaction system can be appropriately used.

While the typical steps have been explained in the above, the method of the present invention is applicable to any assay heretofore practiced using a solid phase. In an immunocomplex transfer assay (Ishikawa S. et al., J. Clin. Lab. Anal. 12, 179 (1998)), the inventive method can be used in both the reaction to trap the analyte on a first solid phase, and the reaction to transfer the immunecomplex from the first solid phase to a second solid phase. That is, the assay system may be homogeneous or heterogeneous, and a sandwich method or a competitive method can be used. The detection method may be any, such as colorimetric analysis, fluorescence detection, measurement of light emission, radioactive determination and the like, and is free of any limitation.

The present invention is explained in more detail by way of Examples in the following.

EXAMPLE 1

In this Example, the inventive method was used for the reaction to trap an analyte in a certain amount of a solution on a solid phase, in order to directly show the characteristic features of the present invention. The details of purification and preparation of each substance and mental steps are as follows.

(1) Buffers:

The following buffers were mainly used in the tests.

Buffer A:0.1 mol/l sodium phosphate buffer, pH 7.0, 5 mmol/l ethylenediamine-tetraacetic acid (EDTA)

Buffer B:0.1 mol/l sodium phosphate buffer, pH 6.0, 5 mmol/l ethylenediamine-tetraacetic acid (EDTA)

Buffer C: 0.01 mol/l sodium phosphate buffer, pH 7.0, 1 g/l bovine serum albumin (action V, Intergen Co., New York), 1 mmol/l magnesium chloride, 0.1 mol/l sodium chloride, 1 g/l sodium azide Buffer D: Buffer C except bovine serum albumin concentration is 0.1 g/l (2) Preparation of affinity-purified (anti-2,4-dinitrophenyl) IgG insolubilized solid phase:

A rabbit (anti-2,4-dinitorophenyl-bovine serum albumin) antibody (IgG) solution was adsorbed on a 2,4-dinitrophenyl-bovine serum albumin column and eluted at pH 2.5 by a known method (Hashida et al., Anal. Lett., 16, 31 (1983)). The affinity-purified anti-2,4-dinitrophenyl IgG was insolubilized on a polystyrene ball (diameter 6.35 mm, Immunochemical Corp., Okayama, Japan) and a polystyrene test tube (12×75 mm, Maxisorp 444202, Nunc Inc., Roskilde, Denmark) according to the method in the previously reported publication (Ishikawa et al., Scand. J. Immunol., ibid.) The solution used had an IgG concentration of 50 µg/ml, and 600 µl thereof was used per one polystyrene test tube.

(3) Preparation of 2,4-dinitrophenyl-β-D-galactosidase:

Buffer A (450 µl containing 5 mmol/l εN-2,4-dinitrophenyl-L-lysine (Tokyo Kasei Kogyo, Tokyo, Japan) and N,N-dimethylformamide (50 µl, containing 30 mmol/l N-succinimidyl-6-maleimidohexanoate (Dojindo Labolatories, Kumamoto, Japan) were mixed and reacted at 30° C. for 30 minutes. The obtained 6-maleimidohexanoyl•εN-2,4-dinitrophenyl-L-lysine (7.5 µl, 22.5 nmol) and Buffer B (300 µl, containing *Escherichia coli*-derived β-D-galactosidase (2.7 mg, 5 nmol, Boehringer Mannheim, Mannheim, Germany)) were reacted at 30° C. for 30 minutes. Then, 0.1 mol/l sodium phosphate buffer pH 6.0, 193 µl) was added to the reaction mixture, and 2,4-dinitrophenyl-β-D-galactosidase was purified by a Sephadex G-50 (Fine, Pharmacia LKB Biotechnology Inc., Upsula, Sweden) column (1.1×5.3 cm) according to the gel filtration chromatography method in the previously reported publication (H. S. Penefsky et al., Methods in Enzymology, 56, 527 (1979)). The buffer used for the gel filtration was 10 mmol/l sodium phosphate buffer, pH 7.0, containing 0.1 mol/l sodium chloride. The average number of 2,4-dinitrophenyl groups introduced into one molecule of β-D-galactosidase was 3.9.

(4) Activity assay of β-D-galactosidase:

For the assay of β-D-galactosidase, a reaction was carried out according to a known method (Imagawa et al., Ann. Clin. Biochem., 21, 310 (1984)) using 4-methylumbelliferyl-β-D-galactoside as a substrate, and the resulting 4-methylumbelliferone was assayed for fluorescence intensity by a spectrophotofluorometer (RF-510, Shimadzu Corporation, Kyoto, Japan). The fluorescence value was compensated for based on the fluorescence intensity of 0.1 mol/l glycine-sodium hydroxide buffer (pH 10.3) containing 1×10$^{-8}$ mol/l 4-methylumbelliferone as 100.

(5) Binding of 2,4-dinitrophenyl-β-D-galactosidase to affinity-purified (anti-2,4-dinitrophenyl) IgG insolubilized polystyrene ball:

Buffer C containing 115.5 amol of 2,4-dinitrophenyl-β-D-galactosidase (15 µl, concentration: 7.7 amol/µl) was placed on the bottom of a 14×54 mm styrol test tube, and one affinity-purified (anti-2,4-dinitrophenyl) IgG insolubilized polystyrene ball (diameter 6.35 mm) was added thereto, which was followed by a shaking reaction at room temperature for 1.25 minutes and 2.5 minutes. For shaking, the styrol test tube was stood in a 15×15×20 (height) mm frame and shaken at 140 reciprocations per minute at a 2.5 cm amplitude. Then, the polystyrene ball was washed 4 times with Buffer D (2 ml), and the activity of β-D-galactosidase bound to the polystyrene ball was assayed by reaction with the substrate at room temperature for 5 minutes. The proportion (%) of 2,4-dinitrophenyl-β-D-galactosidase that bound to the polystyrene ball during the respective time for shaking, from 115.5 amol first contained in the buffer, is shown in Table 1 and FIG. 4.

(6) Binding of 2,4-dinitrophenyl-β-D-galactosidase to affinity-purified (anti-2,4-dinitrophenyl) IgG insolubilized polystyrene test tube:

To an anti-2,4-dinitrophenyl IgG insolubilized polystyrene test tube (12×75 mm) was added Buffer C containing 115.5 amol of 2,4-nitrophenyl-β-D-galactosidase (15 µl, concentration: 7.7 amol/µl), and the tube was rotated at about 30 rotations a minute so that the surface where IgG had been insolubilized contacted the reaction liquid alternately in a uniform manner to allow reaction at room temperature for 1.25 minutes and 2.5 minutes. Then, the inside of the tube was washed twice with Buffer D (0.7 ml) and twice with 0.9 ml thereof. The activity of β-D-galactosidase bound to the polystyrene test tube was assayed by reaction at room temperature for 5 minutes. The proportion (%) of 2,4-dinitrophenyl-β-D-galactosidase that bound to the polystyrene test tube during each shaking reaction, from the initially contained 115.5 amol in the first buffer, is shown in Table 1 and FIG. 4.

COMPARATIVE EXAMPLE 1

In this Comparative Example, an analyte present in a certain amount of solution as in Example 1 was trapped on a solid phase in such a manner that the entire solid phase came into contact with the reaction liquid. The details of purification and preparation of each substance and experimental steps are as shown in Example 1 except the following.

Binding of 2,4-dinitrophenyl-β-D-galactosidase to affinity-purified (anti-2,4-dinitrophenyl) IgG insolubilized polystyrene ball:

Buffer C containing 115.5 amol of 2,4-dinitrophenyl-β-D-galactosidase (150 µl concentration: 0.77 amol/µl) was placed in a 10×75 mm glass test tube, and one affinity-purified (anti-2,4-dinitrophenyl) IgG insolubilized polystyrene ball (diameter 6.35 mm) was added therein, which was followed by shaking at room temperature for 1.25 minutes and 2.5 minutes to allow reaction, wherein 150 µl was a necessary minimum volume for immersing the entire polystyrene ball having a diameter of 6.35 mm in the reaction liquid. For shaking, the glass test tube was stood in a 14×14 mm frame and shaken at 170 reciprocations per minute at a 2.5 cm amplitude. Then, the polystyrene ball was washed 4 times with Buffer D (2 ml), and the activity of β-D-galactosidase bound to the polystyrene ball was assayed by reaction with the substrate at room temperature for 5 minutes. The proportion (%) of 2,4-dinitrophenyl-β-D-galactosidase that bound to the polystyrene ball during the respective time for shaking, from 115.5 amol first contained in the buffer, is shown in Table 1 and FIG. 4. Using buffer C (150 µl) containing 1155 amol (10-fold amount) of 2,4-dinitrophenyl-β-D-galactosidase (the concentration being the same as in Example 1 and 7.7 amol/µl), the same procedure as above was followed. The relation of the reaction time and the proportion (%) of 2,4-dinitrophenyl-β-D-galactosidase that bound to the polystyrene ball, from 1155 amol first contained in the buffer, is shown in Table 1 and FIG. 4.

TABLE 1

Binding of 2,4-dinitrophenyl-β-D-galactosidase to anti-2,4-dinitrophenyl IgG insolubilized solid phase

| Experiment | Solid phase [size of test tube in brackets] | Volume of buffer (μl) | Moles of 2,4-dinitrophenyl-β-D-galactosidase (amol) [concentration (amol/μl) in brackets] | Percentage (%) of 2,4-dinitrophenyl-β-D-galactosidase molecules trapped on surface of solid phase Reaction time (min) | |
|---|---|---|---|---|---|
| | | | | 1.25 | 2.50 |
| Example 1 | Polystyrene ball, diameter 6.35 mm [14 × 54 mm] | 15 | 115.5 [7.7] | 78 | 100 |
| | Polystyrene tube [12 × 75 mm] | 15 | 115.5 [7.7] | 84 | 96 |
| Comparative Example 1 | Polystyrene ball, diameter 6.35 mm [10 × 75 mm] | 150 | 115.5 [0.77] | 12 | 19 |
| | | 150 | 1155 7.7 | 11 | 16 |

EXAMPLE 2

In this Example, the inventive method was used as in Example 1 for the reaction to trap an analyte on a solid phase using a centrifugal cup type solid phase. The details of purification and preparation of each substance and experimental steps are as shown in Example 1 except the following.

(1) Preparation of affinity-purified (anti-2,4-dinitrophenyl) IgG insolubilized polystyrene cup:

A 0.1 mol/l sodium phosphate buffer (pH 7.5, 5 ml) containing 10 μg/ml affinity-purified (anti-2,4-dinitrophenyl) Ig was added to a polystyrene cup (FIG. 3, D) and the cup was stood at 4° C. overnight The antibody solution was removed and Buffer C (10 ml) was added to the polystyrene cup, which was allowed to stand at 4° C. until use.

(2) Binding of 2,4-dinitrophenyl-β-D-galactosidase to affinity-purified (anti-2,4-dinitrophenyl) IgG insolubilized polystyrene cup:

An affinity-purified (anti-2,4-dinitrophenyl) IgG insolubilized polystyrene cup was washed with Buffer C before use and subjected to the following two tests.

Manual method: Buffer C (150 μl) containing 2,4-dinitrophenyl-β-D-galactosidase (1.155 pmol) was added to the antibody insolubilized polystyrene cup, and a pool of reaction liquid was manually moved on the antibody insolubilized surface, thereby allowing reaction at room temperature for 1 minute, 2 minutes and 4 minutes. Then, the residual β-D-galactosidase activity in the reaction liquid was assayed and the proportion (%) of the molecules trapped on the antibody insolubilized surface from the 2,4-dinitrophenyl-β-D-galactosidase added in the polystyrene cup was determined.

Figure 5:
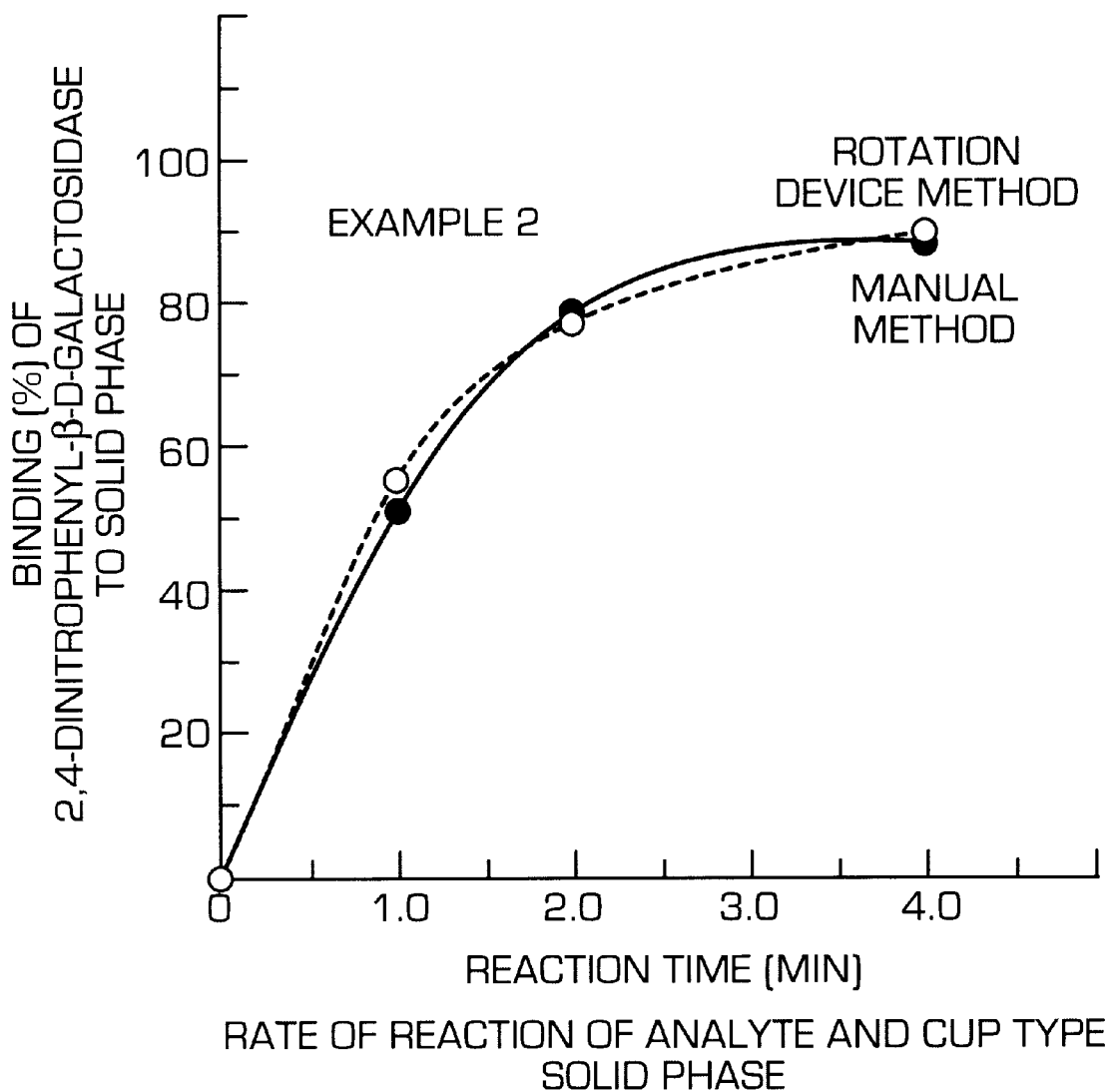
FIG. 5 is a graph showing the relation of reaction time and reaction rate (percentage) of the inventive method using a cup type solid phase in a reaction between an analyte contained in a certain amount of a solution and a substance on the solid phase that specifically binds to said analyte.

Rotation device method: The antibody insolubilized polystyrene cup was fixed with its central axis aligned with the direction of rotational axis of the rotation device. In the same manner as in the manual method, Buffer C (150 μl) containing 2,4-dinitrophenyl-β-D-galactosidase (1.155 pmol) was added and the cup was rotated by the rotation device. The rotation was stopped when the centrifugal force moved the pool of reaction liquid to the side of the cup where the antibody had been insolubilized, to allow the pool of the reaction liquid to descend. This step was repeated, and in the same manner as in the manual method, the proportion (%) of the molecules trapped on the antibody insolubilized surface was determined after reaction for 1 minute, 2 minutes and 4 minutes. The results are shown in Table 2 and FIG. 5.

TABLE 2

Binding of 2,4-dinitrophenyl-β-D-galactosidase to anti-2,4-dinitrophenyl IgG insolubilized solid phase

| Experiment | Reaction method | Percentage (%) of 2,4-dinitrophenyl-β-D-galactosidase molecules trapped on surface of polystyrene cup solid phase Reaction time (min) | | | |
|---|---|---|---|---|---|
| | | 0 | 1 | 2 | 4 |
| Example 2 | Manual method | 0 | 51 | 78 | 88 |
| | Rotation device method | 0 | 55 | 77 | 89 |

EXAMPLE 3

In this Example, the inventive method was used to assay HIV-1, p24 antigen in a test solution using anti-p24 antibody insolubilized polystyrene ball solid phase (diameter 6.35 mm). The details of purification and preparation of each substance and experimental steps are as mentioned above except the following.

(1) Preparation of gene recombinant HIV-1, p24 (rp24):

A gene recombinant HIV-1, p24 (rp24) was prepared by amplifying p24 DNA fragment from a DNA derived from HIV-1 isolation strain by a polymerase chain reaction method (PCR method), introducing the DNA fragment into a plasmid, expression thereof as a fusion protein with a maltose binding protein (MBP) by *Escherichia coli*, purifying same by various protein purification methods, cleaving rp24 and MBP by biotinyl Xa factor, and removing the biotinyl Xa factor by a streptavidin column using a kit provided by Boehringer Mannheim (Mannheim, Germany) according to the operation manual of the manufacturer. The purity of the purified rp24 was confirmed by electrophoresis.

(2) Preparation of 2,4-dinitrophenyl-biotinyl-bovine serum albumin-affinity-purified (anti-HIV-1, p24) Fab':

Rabbits were immunized with purified rp24 by the method of the previously reported publication (Hashida et al., J. Clin. Microbiol., 33, 298 (1995)) to obtain antisera. According to a known method (Hashida et al., J. Clin. Lab. Anal., 10, 302 (1996)), 2,4-dinitrophenyl-biotinyl-bovine serum albumin-affinity-purified (anti-HIV-1, p24) Fab' was prepared.

(3) Preparation of 2,4-dinitrophenyl-biotinyl-bovine serum albumin-affinity-purified (anti-HIV-1, p24) Fab' insolubilized polystyrene ball:

Buffer C (15 μl) containing 200 fmol of 2,4-dinitrophenyl-biotinyl-bovine serum albumin-affinity-purified (anti-HIV-1, p24) Fab' was placed on the bottom of a 14×54 mm styrol test tube and thereto was added one affinity-purified (anti-2,4-dinitrophenyl) IgG insolubilized polystyrene ball (diameter 6.35 mm). The tube was shaken for 10 minutes in the same manner as in Example 1(5). Then, the polystyrene ball was washed.

(4) Preparation of mouse (anti-HIV-1, p24) monoclonal Fab'-β-D-galactosidase:

The preparation involved use of mouse (anti-p24) monoclonal antibody purchased from Innogenetics (Belgium) and the method of the previously reported publication (Hashida et al., J. Clin. Lab. Anal., (1996), ibid.).

Figure 6:
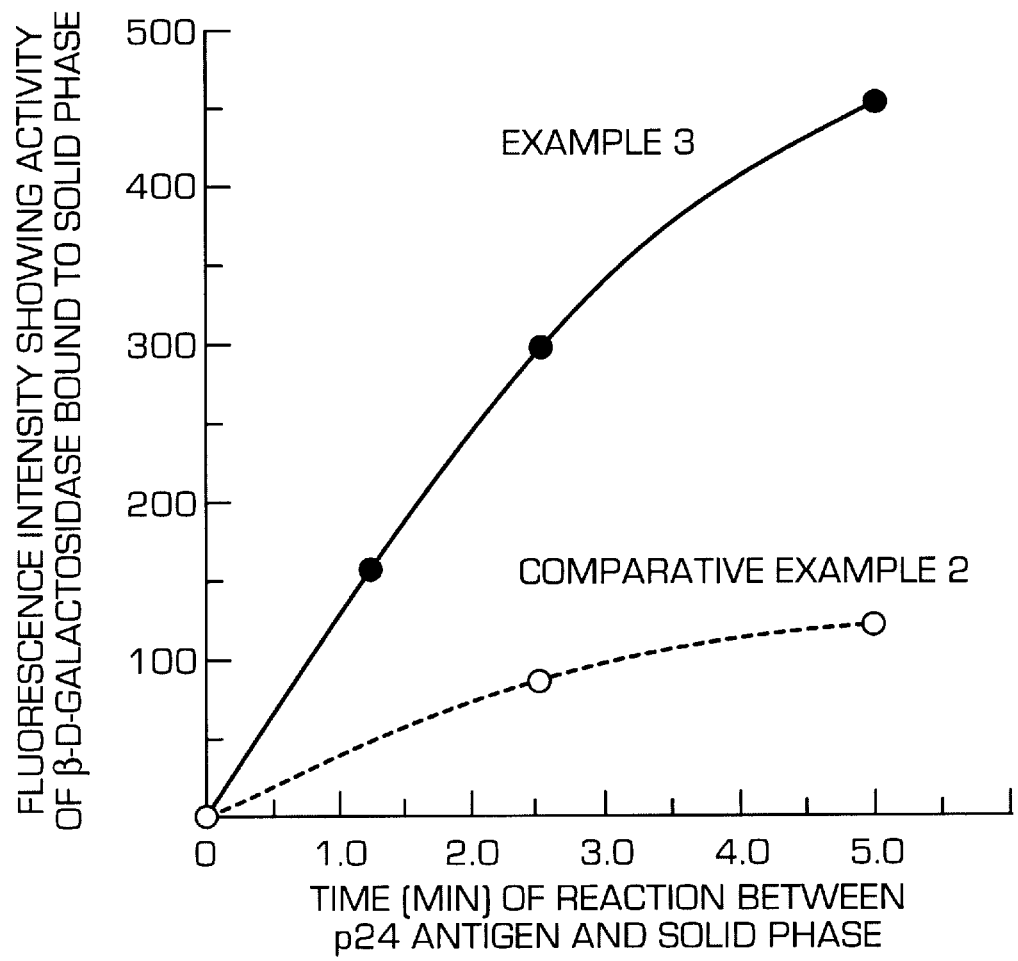
FIG. 6 is a graph showing the relation of reaction time and fluorescence intensity of the inventive method and a conventional method in an assay system comprising trapping HIV-1, p24 antigen in a test solution on a solid phase coated with an anti-p24 antibody.

(5) Assay of HIV-1, p24 antigen in a test solution:

Buffer C (15 μl) containing 300 amol of HIV-1, p24 antigen was placed on tile bottom of a 14×54 mm styrol test tube and thereto was added a 2,4-dinitrophenyl-biotinyl-bovine serum albumin-affinity-purified (anti-HIV-1, p24) Fab'insolubilized polystyrene ball (diameter 6.35 mm). The test tube was shaken for 1.25 minutes, 2.5 minutes and 5 minutes in the same manner to allow reaction, and the polystyrene ball was washed as in Example 1(5). Then, the washed polystyrene ball was transferred into a 14×54 mm styl test tube containing Buffer C (15 μl) containing 40 fmol of mouse (anti-HIV-1, p24) monoclonal Fab'-β-D-galactosidase and shaken for 5 minutes to allow reaction, which was followed by washing. The activity of β-D-galactosidase bound to the polystyrene ball was assayed as mentioned above by reaction for 30 minutes. The relation of the reaction time of the first shaking reaction and the activity assay of β-D-galactosidase bound to the polystyrene ball is shown in Table 3 and FIG. 6.

COMPARATIVE EXAMPLE 2

In this Comparative Example, a solution containing a certain amount of HIV-1, p24 antigen and an anti-p24 antibody insolubilized polystyrene ball were reacted in a conventional manner, wherein the entire polystyrene ball was in contact with the reaction liquid. The details of purification and preparation of each substance and experimental steps are as mentioned above except the below-mentioned.

Assay of HIV-1, p24 antigen in a test solution:

Buffer C (150 μl) containing 300 amol of HIV-1, p24 antigen was placed ina 10×75 mm glass test tube, and one 2,4-dinitrophenyl-biotinyl-bovine serum albumin-affinity-purified (anti-HIV-1, p24) Fab' insolubilized polystyrene ball (diameter 6.35 mm) was added thereto. In the same manner as in Comparative Example 1, the test tube was shaken for 2.5 minutes and 5 minutes, which was followed by washing of the polystyrene ball as in Example 1. Then, the washed polystyrene ball was reacted with mouse (anti-HIV-1, p24) monoclonal Fab'-β-D-galactosidase in the same manner as in Example 3(5), and the activity of β-D-galactosidase bound to the polystyrene ball was assayed. The relation of the reaction time of the first shaking reaction and the activity assay of β-D-galactosidase bound to the polystyrene ball is shown in Table 3 and FIG. 6.

TABLE 3

Binding of HIV-1, p24 antigen to 2,4-dinitrophenyl-biotinyl-bovine serum albumin-affinity-purified (anti-p24) Fab' insolubilized solid phase

| | p24 antigen per tube | of p24 antigen solution | Size of test | Time of reaction between p24 antigen and solid phase (min) | | |
|---|---|---|---|---|---|---|
| Experiment | (amol) | (μl) | tube (mm) | 1.25 | 2.5 | 5.0 |
| Example 3 | 300 | 15 | 14 × 54 | 155 | 299 | 454 |
| Comparative Example 2 | 300 | 150 | 10 × 75 | — | 86 | 122 |

Volume / Fluorenscence intensity showing activity of β-D-galactosidase bound to solid phase

EXAMPLE 4

In this Example, the inventive method was used to trap an anti-HIV-1, p17 antibody in a test solution on a p17 antigen insolubilized polystyrene ball solid phase (diameter 6.35 mm) and to detect using an enzyme labeled p17. The details of purification and preparation of each substance and experimental steps are as mentioned above except the below-mentioned.

(1) Preparation of maltose binding protein-fused gene recombinant HIV-1, p17 antigen and gene recombinant HIV-1, p17 antigen:

The maltose binding protein (MBP)-fused gene recombinant p17 (rp17) was expressed by *Escherichia coli* using a p17 DNA fragment amplified from HIV-1 isolation strain-derived DNA by a PCR method in the same manner as in the preparation of rp24 as described in Example 3(1), and purified. In the same manner as in the preparation of rp24 as described in Example 3(1), MBP-rp17 was cleaved with a specific enzyme to prepare rp17. The purified MBP-rp17 and rp17 were confirmed to be pure by electrophoresis.

(2) Preparation of 2,4-dinitrophenyl-MBP-rp17:

MBP-rp17 into which a thiol group had been introduced using N-succinimidyl-S-acetylmercaptoacetate and εN-2,4-dinitrophenyl-L-lysine into which a maleimide group had been introduced using N-succinimidyl 6-maleimidohexanoate were reacted by a known method (Eiji Ishikawa, Ultrasensitive enzyme immunoassay, Gakkai Shuppan Center, p. 311 (1993)) for preparation. The average number of 2,4-dinitrophenyl groups incorporated into one molecule of MBP-rp17 as calculated by the method of Eisen et al. (Eisen et al., J. Immunol., 73, 296 (1954)) based on the absorbance at 280 nm and 360 nm was 3.9.

(3) Preparation of β-D-galactosidase-rp17:

Mercaptoacetyl-rp17 and maleimido-β-D-galactosidase were reacted by a known method (Hashida et al., J. Clin. Lab. Anal., 7, 353 (1993)) for preparation.

(4) Preparation of 2,4-dinitrophenyl-MBP-rp17 insolubilized polystyrene ball:

Buffer C (15 μl) containing 800 fmol of 2,4-dinitrophenyl-MBP-rp17 was placed on the bottom of a 14×54 mm styrol test tube and one affinity-purified (anti-2,4-dinitrophenyl) IgG insolubilized polystyrene ball (diameter 6.35 mm) was added therein. The test tube was shaken for 5 minutes in the same manner and the polystyrene ball was washed as in Example 1(5).

(5) Assay of anti-p17 antibody in a test solution:

Sera from HIV-1 infected patients were diluted $2 \times 10^4$ fold, $2 \times 10^5$ fold and $2 \times 10^6$ fold with sera from non-infected individuals, and 10 μl therefrom and Buffer C (5 μl) were placed on the bottom of a 14×54 mm styrol test tube. Thereto was added a 2,4-dinitrophenyl-MBP-rp17 insolubilized polystyrene ball (diameter 6.35 mm) prepared above, and the test tube was shaken for 5 minutes in the same manner as in Example 1(5). Thereto was added Buffer C (10 μl) containing 40 fmol of β-D-galactosidase-rp17 and the test tube was shaken for 10 more minutes. In the same manner as in Example 1(5), the polystyrene ball was washed, and the activity of β-D-galactosidase bound to the polystyrene ball was assayed as mentioned above by reaction for 10 minutes. The activity assay value of β-D-galactosidase bound to the polystyrene ball when diluted sera were used are shown in Table 4.

COMPARATIVE EXAMPLE 3

In this Comparative Example, anti-HIV-1, p17 antibody in the test sera from HIV-1 infected patients, that had been diluted with sera from non-infected individuals, was detected by a prior art technique, western blotting.
Detection of anti-HIV-1, p17-antibody by western blot:

The test sera from HIV-1 infected patients as used in Example 4, that had been diluted with sera from non-infected individuals (additionally including sera diluted $1\times10^3$ fold and $3\times10^2$ fold) were subjected to detection of anti-HIV-1, p17 antibody according to the method of the previously reported publication (Hashida et al., J. Clin. Lab. Anal. (1993) (ibid.)) using an Ortho HIV western blot kit (Ortho Diagnostic Systems, New Jersey, USA). The detection results are shown in Table 4 together with the results of Example 4.

TABLE 4

Assay of anti-HIV-1, p17 IgG

| Experiment | Sera from non-HIV-1 individuals | Dilution ratio of sera from HIV-1 patient with sera from non-infected individuals | | | | |
|---|---|---|---|---|---|---|
| | | $2\times10^6$ | $2\times10^5$ | $2\times10^4$ | $1\times10^3$ | $3\times10^2$ |
| Example 4 (fluorescence intensity showing β-D-galactosidase activity) | 2.8 | 4.3 | 17 | 164 | — | — |
| Comparative Example 3 (Western blotting) | Negative | Negative | Negative | Negative | Negative | Positive |

—: not determined

EXAMPLE 5

In this Example, anti-HIV-1, p17 antibody was assayed by the method of the present invention using a technique described in Ultrasensitive enzyme immunoassay, Eiji Ishikawa, ibid., wherein two kinds of solid phases were used to reduce assay backgrounds so that ultrahigh sensitivity assay of analyte can be performed. The details of purification and preparation of each substance and experimental steps are as mentioned above except the following.
(1) Preparation of affinity-purified (anti-human Ig Y chain) IgG insolubilized polystyrene tube:

A 0.1 mol/l sodium phosphate buffer (pH 7.5, 400 μl) containing affinity-purified (anti-human IgG Y chain) IgG (10 μg/ml) and 1 g/l sodium azide was placed in a polystyrene tube (12×75 mm, Maxisorp 444202, Nunc Inc., Denmark) and the tube was allowed to stand overnight at 4° C. Then, the tube was washed with Buffer C. This buffer (500 μl) was added and the tube was preserved before use at 4° C.
(2) Assay of anti-p17 antibody in a test solution:

Test sera (10 μl) from HIV-1 infected patients, that had been diluted in the same manner as in Example 4, were mixed with Buffer C (12 μl, NaCl concentration 0.62 mol/l) containing 100 fmol of 2,4-dinitrophenyl-MBP-rp17, 100 fmol of β-D-galactosidase-rp17 and inactive β-D-galactosidase (5 μg, mutain, Boehringer Mannheim, Germany) in a 14×54 mm styrol tube and allowed to stand for 10 minutes. Thereto was added one above-mentioned affinity-purified (anti-2,4-dinitrophenyl) IgG insolubilized polystyrene ball (diameter 6.35 mm) and the tube was shaken for 5 minutes in the same manner as in Example 1(5) to allow reaction. The polystyrene ball was washed 4 times with Buffer D (2 ml) and the ball was placed in an affinity-purified (anti-human IgG Y chain) IgG insolubilized polystyrene tube containing Buffer C (30 II) containing 1 mmol/l εN-2,4-dinitrophenyl-L-lysine, and the tube was shaken for 10 minutes to allow reaction. For shaking, the polystyrene tube was set in a 15×30×20 (depth) mm frame and shaken at 150 reciprocations per minute at a 2.5 cm amplitude. Then, the polystyrene tube was washed in the same manner as in Example 1(6), and the activity of β-D-galactosidase bound to the polystyrene tube was assayed by reaction for 60 minutes.

The liquid amount of the substrate solution was half the amount used in Example 1, i.e., 75 μl, and the tube was rotated in such a manner that the inner surface, where anti-human IgG Y chain IgG had been insolubilized, came into continuous contact with the substrate solution. The activity assay values of β-D-galactosidase bound to the polystyrene tube upon assay of each diluted serum are shown in Table 5.

EXAMPLE 6

In this Example, anti-HIV-1, p17 antibody was assayed according to the inventive method using ultrasensitive enzyme immunoassay as in Example 5. The assay principle was different from Example 5. The details of purification and preparation of each substance and experimental steps are as mentioned above except the following.
Assay of anti-p17 antibody in a test solution:

Test sera (10 μl) from HIV-1 infected patients as used in Example 5, that had been diluted with sera from non-infected individuals and Buffer C (6 μl, NaCl concentration 0.73 mol/l) containing 5 μg of inactive β-D-galactosidase (mutain), were placed on the bottom of a 14×54 mm styrol tube. Thereto was added one 2,4-dinitrophenyl-MBP-rp17 insolubilized polystyrene ball (diameter 6.35 mm) and the tube was shaken for 5 minutes to allow reaction in the same manner as in Example 1(5). Thereto was added Buffer C (10 [l, NaCl concentration 0.4 mol/l) containing 200 fmol of β-D-galactosidase-rp17, and the tube was shaken for 5 minutes to allow reaction in the same manner as above. The polystyrene ball was washed in the same manner as in Example 1(5), and, in the same manner as in Example 5(2), the polystyrene ball was placed in an affinity-purified (anti-human IgG Y chain) IgG insolubilized polystyrene tube (12×75 mm) together with εN-2,4-dinitrophenyl-L-lysine, and the tube was shaken for 5 minutes. The polystyrene tube was washed and the activity of β-D-galactosidase bound to the polystyrene tube was assayed by reaction for 60 minutes as in Example 5(2). The activity assay values of β-D-galactosidase bound to the polystyrene tube upon assay of diluted sera are shown in Table 5.

EXAMPLE 7

In this Example, the same assay as in Example 6 was performed in a partially different reaction time frame in an attempt to shorten the total assay time. The details of purification and preparation of each substance and experimental steps are as mentioned above except the following. Assay of anti-p17 antibody in a test solution:

The steps of Example 6 were followed except that the reaction time with β-D-galactosidase-rp17 was changed from 5 minutes to 10 minutes, the reaction time in the polystyrene tube was changed from 5 minutes to 10 minutes and the activity assay time of β-D-galactosidase was changed from 60 minutes to 30 minutes. The activity assay values of β-D-galactosidase bound to the polystyrene tube upon assay of diluted sera are shown in Table 5.

COMPARATIVE EXAMPLE 4

In this Comparative Example, anti-HIV-1, p17 antibody was assayed by conventional ultrasensitive enzyme immunoassay. The details of purification and preparation of each substance and experimental steps are as mentioned above except the following.

(1) Preparation of affinity-purified (anti-2,4-dinitrophenyl) IgG insolubilized polystyrene ball (diameter 3.2 mm) and affinity-purified (anti-human IgG Y chain) IgG insolubilized polystyrene ball (diameter 3.2 mm):

According to the method of Example 1(2), a polystyrene ball (diameter 3.2 mm, Immunochemical Inc., Okayama, Japan) was immersed in Buffer A containing 50 μg /ml of affinity-purified (anti-2,4-dinitrophenyl) IgG or affinity-purified (anti-human IgG Y chain) IgG at 4° C. for 24 hours to allow physical adsorption. Both polystyrene balls were discriminated by using a colored polystyrene ball for insolubilization of affinity-purified (anti-2,4-dinitrophenyl) IgG and a white polystyrene ball for insolubilization of affinity-purified (anti-human IgG Y chain) IgG.

(2) Assay of anti-p17 antibody in a test solution:

Test sera from HIV-1 infected patients, that had been diluted as used in Example 4, were assayed for anti-HIV-1, p17 antibody according to the method of the previously reported publication (Setsuko Ishikawa et al., J. Clin. Lab. Anal., 12, 179 (1998)) except that 2,4-dinitrophenyl-MBP-rp17 was used instead of 2,4-dinitrophenyl-bovine serum albumin-rp17. The test sample (10 μl) was reacted with Buffer C (140 μl, containing 0.4 mol/l sodium chloride) containing 100 fmol of 2,4-dinitrophenyl-MBP-rp17, 100 fmol of β-D-galactosidase-rp17 and 50 μg of inactive β-D-galactosidase (mutain, ibid.) in a 10×75 mm lass test tube at room temperature for 30 minutes, wherein the total volume of the reaction liquid was 150 μl and the polystyrene ball was completely immersed in the reaction liquid. After the reaction, two affinity-purified (anti-2,4-dinitrophenyl) IgG insolubilized colored polystyrene balls (diameter 3.2 mm) were added and the tube was shaken in the same manner as in Comparative Example 1 for 60 minutes. Any colored polystyrene ball was washed. The two washed colored polystyrene balls were placed in a 10×75 mm glass test tube together with Buffer C (150 μl) containing 1 mmol/l εN-2, 4-dinitrophenyl-L-lysine and two white affinity-purified (anti-human IgG Y chain) IgG insolubilized polystyrene balls (diameter 3.2 mm), and the test tube was shaken in the same manner as in Comparative Example 1 at room temperature for 60 minutes. In the same manner as in Example 1(5), the white polystyrene balls were washed and the activity of β-D-galactosidase bound to the white polystyrene balls was assayed by reaction at room temperature for 60 minutes. The activity assay values of β-D-galactosidase bound to the white polystyrene balls, when diluted sera were used, are shown in Table 5, along with the results of Examples 5–7.

TABLE 5

Assay of anti-HIV-1, p17 IgG

| Experiment | Total immunological reaction time (min) | Enzyme activity assay time (min) | Sera from non-HIV-1 individuals | Fluorescence intensity showing β-D-galactosidase activity — Dilution ratio of sera from HIV-1 patient with sera from non-infected individuals | | |
|---|---|---|---|---|---|---|
| | | | | $2 \times 10^6$ | $2 \times 10^5$ | $2 \times 10^4$ |
| Example 5 | 25 | 60 | 0.20 | 3.9 | 32 | 373 |
| Example 6 | 15 | 60 | 0.00 | 4.7 | 47 | 439 |
| Example 7 | 25 | 30 | 0.00 | 3.5 | 38 | 328 |
| Comparative Example 4 | 150 | 60 | 0.25 | 4.1 | 35 | 365 |

EXAMPLE 8

In this Example, the inventive method was used for an activity assay reaction of the enzyme trapped on the surface of an insoluble carrier, so as to show that the inventive thin layer circulation liquid phase method is effective for the enzyme reaction to detect a label on a carrier in an enzyme immunoassay. The details of purification and preparation of each substance and experimental steps are as mentioned above except the following. (1) Preparation of 2,4-dinitrophenyl-β-D-galactosidase bound polystyrene bail:

One affinity-purified (anti-2,4-dinitrophenyl) IgG bound polystyrene ball (diameter 6.35 mm) and Buffer C (150 μl) containing 200 amol of 2,4-dinitrophenyl-β-D-galactosidase were added to a 14×54 mm styrol test tube. The test tube was shaken for 10 minutes for incubation at room temperature.

(2) Assay of enzyme activity of β-D-galactosidase bound to polystyrene ball

A 2,4-dinitrophenyl-β-D-galactosidase bound polystyrene ball was washed with Buffer C, and reacted by shaking with Buffer D (20 μl) containing 0.1 mmol/l 4-methylumbelliferyl-β-D-galactoside in a 14×54 mm styrol test tube in the same manner as in Example 1(5) for 10 minutes at room temperature to allow reaction. Then, a 0.1 mol/l glycine-sodium hydroxide buffer (pH 10.3, 2.5 ml) was added to stop the reaction. After the reaction, fluorescence intensity was assayed at an excitation wavelength of 360 nm and fluorescence wavelength of 450 nm. The fluorescence intensity was compensated for based on the fluorescence intensity of $1 \times 10^{-8}$ mol/l 4-methylumbelliferone solution dissolved in 0.1 mol/l glycine-sodium hydroxide buffer (pH 10.3) as 100. A similar test was carried out using a polystyrene ball free of binding with 2,4-dinitrophenyl-β-D-galactosidase. The fluorescence intensity in the presence or absence of 2,4-dinitrophenyl-β-D-galactosidase, as well as the ratio of the presence/absence, are shown in Table 6.

COMPARATIVE EXAMPLE 5

In this Comparative Example, an activity assay reaction of an enzyme trapped on the surface of an insoluble carrier as in Example 8 was carried out in a conventional manner, where the entire carrier was in contact with the substrate solution. The details of purification and preparation of each substance and experimental steps are as mentioned above except the following.

Enzyme activity assay of β-D-galactosidase bound to polystyrene ball:

An assay was performed as in Example 8 except that the amount of Buffer D containing 0.1 mmol/l 4methylumbelliferyl-β-D-galactoside was 150 μl. The fluorescence intensity in the presence or absence of 2,4-dinitrophenyl-β-D-galactosidase, as well as the ratio of the presence/absence, are shown in Table 6, along with the results of Example 8.

TABLE 6

Activity assay of 2,4-dinitrophenyl-β-D-galactosidase bound to affinity-purified (anti-2,4-dinitrophenyl) IgG insolubibzed polystyrene ball (diameter 6.35 mm)

| Experiment | Addition of anti-DNP antibody insolubilized polystyrene balls | DNP-Gal addition (amol) | Amount of substrate liquid (μl) | Fluorescence intensity | Ratio of fluorescence intensity of DNP-Gal addition/ no addition |
|---|---|---|---|---|---|
| Example 8 | – | 0 | 20 | 0.5 | 796/1 |
|  | + | 200 | 20 | 398 |  |
| Comparative | – | 0 | 150 | 3.3 | 121/1 |
| Example 5 | + | 200 | 150 | 399 |  |

DNP: 2,4-dinitrophenyl
Gal: β-D-galactosidase

According to the method of the present invention, the reaction efficiency of a reaction, wherein an analyte in a reaction liquid is trapped on a solid phase, can be markedly improved as compared to conventional methods. As a consequence, a high trapping rate can be achieved by the reaction in a short time. This effect is noticeable not only in a typical antigen-antibody sandwich assay, but also in the immunocomplex transfer assay that the present inventors have developed. The time necessary for an immune reaction to achieve assay sensitivity the same as or greater than a conventional method is 1/10 of the time necessary for a conventional method, or not more than 1/3 of the total assay time. When the inventive method is used for an enzyme immunoassay, the reaction proceeds with a lesser amount of a substrate solution, thereby making the reaction noise due to the reagent itself a quarter or less of a conventional method and the assay sensitivity (signal/noise) several times higher.

According to the method of the present invention, the reaction efficiency can be markedly improved in a reaction wherein an analyte in a reaction liquid is trapped on an insoluble carrier coated with a substance that specifically binds to the analyte. This is because the inventive method enables reaction between the analyte contained in the reaction liquid at high concentrations, and a greater surface area of the solid phase using conventional materials, thereby strikingly increasing the reaction speed. Inasmuch as the analyte is contained in high concentrations, the amount thereof that is trapped on the solid phase increases, thereby improving detection sensitivity. The assay according to the present invention affords advantages in that it requires a short time to reach equilibrium, thus enabling fine reproducibility, it requires a small amount of a substrate solution for the reaction, thereby reducing the amount of reagent and noise due to the reagent, and it increases the assay sensitivity (signal/noise) value (S/N value).

This application is based on application No. 220956/1997 filed in Japan, the content of which is incorporated hereinto by reference.

What is claimed is:

1. An assay method comprising a reaction for trapping an analyte in a reaction liquid, on the surface of an insoluble carrier, by the action of a substance that specifically binds to the analyte, the assay method characterized by the following (A), (B) and (C):

(A) a part of the surface of the carrier being immersed in a pool of the reaction liquid, (B) the remaining part of said surface being wet with the reaction liquid, forming a thin layer of the reaction liquid, and (C) the parts of (A) and (B) above being exchanged with each other during the reaction.

2. The assay method of claim 1, wherein the reaction liquid comprises a test sample.

3. An assay method comprising trapping an analyte on the surface of an insoluble carrier, by the action of a substance that specifically binds to the analyte, introducing an enzyme into said analyte as a label, and reacting a resulting "insoluble carrier-analyte-enzyme" complex in an enzyme reaction liquid comprising a substrate, the assay method characterized by the following (A), (B) and (C):

(A) a part of the surface of the carrier being immersed in a pool of the enzyme reaction liquid, (B) the remaining part of said surface being wet with the enzyme reaction liquid, forming a thin layer of the enzyme reaction liquid, and (C) the parts of (A) and (B) above being exchanged with each other during the reaction.

4. The assay method of claim 3, wherein the enzyme is β-D-galactosidase.

5. The assay method of claim 1 or claim 3, wherein the insoluble carrier is a polystyrene ball, a polystyrene test tube or a polystyrene cup.

6. The assay method of claim 1 or claim 3, wherein the analyte and the substance that specifically binds thereto cause an immunoreaction (antigen-antibody reaction).

7. The assay method of claim 6, wherein the analyte is an HIV (human immunodeficiency virus) antigen or an anti-HIV antibody and the substance that specifically binds thereto is a specific anti-HIV antibody or an HIV antigen, respectively.

* * * * *